(12) United States Patent
Taylor et al.

(10) Patent No.: US 6,306,368 B1
(45) Date of Patent: *Oct. 23, 2001

(54) AEROSOL FORMULATION CONTAINING A PARTICULATE MEDICAMENT

(75) Inventors: Anthony James Taylor; Patricia Kwong Phieu Burnell, both of Ware (GB)

(73) Assignee: Glaxo Group Limited, Greenford (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/198,463

(22) Filed: Nov. 24, 1998

Related U.S. Application Data

(62) Continuation of application No. 08/440,442, filed on May 12, 1995, now Pat. No. 5,919,435, which is a continuation of application No. 08/305,851, filed on Sep. 14, 1994, now abandoned, which is a continuation of application No. 08/039,424, filed as application No. PCT/GB91/01960 on Nov. 7, 1991, now abandoned.

(30) Foreign Application Priority Data

Nov. 9, 1990 (GB) .................................................. 9024365

(51) Int. Cl.$^7$ ..................................................... A61K 9/12
(52) U.S. Cl. .............................. 424/45; 424/46; 514/826; 514/937
(58) Field of Search ..................... 424/45, 46; 514/826, 514/937

(56) References Cited

U.S. PATENT DOCUMENTS

| | | |
|---|---|---|
| 2,868,691 | 1/1959 | Porush et al. |
| 2,885,427 | 5/1959 | Ruh et al. |
| 3,219,533 | 11/1965 | Mullins |
| 3,261,748 | 7/1966 | Larsen |
| 3,897,779 | 8/1975 | Hansen |
| 4,352,789 | 10/1982 | Thiel |
| 5,118,494 * | 6/1992 | Schultz et al. .......................... 424/45 |
| 5,126,123 | 6/1992 | Johnson ................................. 424/45 |
| 5,225,183 * | 7/1993 | Purewal et al. ........................ 424/45 |
| 5,230,884 * | 7/1993 | Evans et al. ........................... 424/45 |
| 5,552,160 * | 9/1996 | Liversidge et al. .................. 424/489 |
| 5,605,674 * | 2/1997 | Purewal et al. ........................ 424/45 |
| 5,653,962 * | 8/1997 | Akehurst et al. ...................... 424/46 |
| 5,674,471 * | 10/1997 | Akehurst et al. ...................... 424/46 |
| 5,688,782 * | 11/1997 | Neale et al. ............................ 424/45 |
| 5,744,123 * | 4/1998 | Akehurst et al. ...................... 424/45 |

FOREIGN PATENT DOCUMENTS

| | | |
|---|---|---|
| 1719443 | 4/1972 | (DE) . |
| 3905726 | 8/1990 | (DE) . |
| 0 372 777 | 6/1990 | (EP) . |
| 452384 | 10/1993 | (EP) . |
| 977934 | 12/1994 | (GB) . |
| 86/04233 | 7/1986 | (WO) . |
| 90/07333 | 7/1990 | (WO) . |

OTHER PUBLICATIONS

Evans et al., *Journal of Pharmacy and Pharmacology*, 40 (1988), 7P.

Clarke et al. *Journal of Pharmacy and Pharmacology*, Supplement 42 (1990), 9P.

"Hoechst on the substitution for FCKW" Position: Sep. 1990, Hoechst Chemikalien.

Meirion Jones, *New Scientist*, pp. 56–60, May 26, 1988.

* cited by examiner

*Primary Examiner*—Raj Bawa
(74) *Attorney, Agent, or Firm*—Bacon & Thomas

(57) ABSTRACT

Aerosol formulations comprising:
(A) A medicament in particulate form and having a surface coating of a surfactant;
(B) A hydrogen-containing fluorocarbon or chlorofluorocarbon propellant; and
(C) A cosolvent having higher polarity than the propellant which cosolvent is present in an amount of up to 5% w/w based upon propellant;
and methods for their preparation.

7 Claims, No Drawings

AEROSOL FORMULATION CONTAINING A PARTICULATE MEDICAMENT

This application is a continuation of U.S. application Ser. No. 08/440,442, filed May 12, 1995, now U.S. Pat. No. 5,919,435, which is a continuation of U.S. application Ser. No. 08/305,851, filed Sep. 14, 1994, now abandoned, which is a continuation of U.S. application Ser. No. 08/039,424, filed Apr. 29, 1993, now abandoned and which is a 371 application of PCT/GB91/01960, filed Nov. 7, 1991.

BACKGROUND OF THE INVENTION

1. Field of the Invention

This invention relates to aerosol formulations of use in the administration of medicaments by inhalation.

2. Description of the Prior Art

The use of aerosols to administer medicaments has been known for several decades. Such aerosols generally comprise the medicament, one or more chlorofluorocarbon propellants and either a surfactant or a solvent, such as ethanol.

The most commonly used aerosol propellants for medicaments have been Freon 11 ($CCl_3F$) in admixture with Freon 12 ($CCl_2F_2$) and Freon 114 ($CF_2Cl.CF_2Cl$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise hydrogen-containing chlorofluorocarbons and fluorocarbons; medicinal aerosol formulations using such propellant systems are disclosed in, for example, EP 0372777. EP 0372777 requires the use of 1,1,1,2-tetrafluoroethane in combination with both a cosolvent having greater polarity than 1,1,1,2-tetrafluoroethane (e.g. an alcohol or a lower alkane) and a surfactant in order to achieve a stable formulation of a medicament powder. In particular it is noted in the specification at page 3, line 7 that "it has been found that the use of Propellant 134a (1,1,1,2-tetrafluoroethane) and drug as a binary mixture or in combination with a conventional surfactant such as sorbitan trioleate does not provide formulations having suitable properties for use with pressurised inhalers".

SUMMARY OF THE INVENTION

We have now surprisingly found that, in contradistinction to this teaching, it is in fact possible to obtain stable dispersions of finely-powdered medicaments together with surfactants in hydrogen-containing fluorocarbon or chlorofluorocarbon propellants such as 1,1,1,2-tetrafluoroethane if the surfactant is present as a dry coating on the particles of medicament and that the stability of the resulting dispersion is enhanced by the presence of small quantities (e.g. up to 5% w/w) of cosolvents having higher polarity than the propellant such as lower alkanols (e.g. ethanol). This is in contrast to the procedure of EP 0372777, where the medicament and surfactant are simultaneously homogenised, e.g. in ethanol, prior to addition of the propellant.

There is thus provided an aerosol formulation comprising:

(A) a medicament in particulate form and having a surface coating of a surfactant;

(B) a hydrogen-containing fluorocarbon or chlorofluorocarbon propellant; and (C) a cosolvent having higher polarity than the propellant which cosolvent is present in an amount of up to 5% w/w based upon propellant.

DETAILED DESCRIPTION OF THE INVENTION

The propellants for use in the invention may be any hydrogen-containing fluorocarbon or chlorofluorocarbon or mixtures thereof having a sufficient vapour pressure to render them effective as propellants. Such propellants include for example $C_{1-4}$hydrogen-containing fluorocarbons and chlorofluorocarbons such as $CH_2ClF$, $CClF_2$—$CHClF$, $CF_3$—$CHClF$, $CHF_2$—$CClF_2$, $CHClF$—$CHF_2$, $CF_3$—$CH_2Cl$, $CHF_2$—$CHF_2$, $CF_3$—$CH_2F$, $CClF_2$—$CH_3$, $CHF_2$—$CH_3$ and $CF_3CHFCF_3$.

Where mixtures of the hydrogen-containing fluorocarbons or chlorofluorocarbons are employed they may be mixtures of the above identified compounds or mixtures, preferably binary mixtures, with other hydrogen-containing fluorocarbons or chlorofluorocarbons for example $CHClF_2$, $CH_2F_2$ and $CF_3CH_3$.

The propellant may additionally contain a volatile saturated hydrocarbon for example n-butane, isobutane, pentane and isopentane. Preferably a single hydrogen-containing fluorocarbon or chlorofluorocarbon is employed as the propellant. Preferably the propellant will be a non-solvent for the medicament. Particularly preferred as propellants are 1,1,1,2-tetrafluoroethane ($CF_3.CH_2F$) and 1,1,1,2,3,3,3-heptafluoro-n-propane ($CF_3.CHF.CF_3$).

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

Cosolvents which may be used include (e.g. $C_{2-6}$) aliphatic alcohols and polyols such as ethanol, ispropanol and propylene glycol. Preferably ethanol will be employed. In general only small quantities (e.g. 0.05–3.0% w/w) are required to improve the stability of the dispersion- the use of quantities in excess of 5% w/w may tend to dissolve the medicament and/or surfactant. Formulations in accordance with the invention preferably contain less than 1% w/w, e.g. about 0.1% w/w, of cosolvent.

Medicaments which may be administered using aerosol formulations according to the invention include any drugs useful in inhalation therapy which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. dilitiazem; antiallergics, e.g. cromolyn; antibiotics, e.g. cephalosporins, penicillins, streptomycin, sulphonamides or tetracyclines; antihistamines, e.g. methapyrilene; anti-inflammatories, e.g. beclomethasone, flunisolide or fluticasone; antitussives, e.g. noscapine; bronchodilators, e.g. ephedrine, epinephrine, isoproterenol, metaproterenol, phenylephrine, phenylpropanolamine, pirbuterol, rimiterol, salbutamol, salmeterol, (−)-4-amino-3,5-dichloro-α-[[[6-[2-(2-pyridinyl)ethoxy]hexyl]amino]methyl]benzenemethanol or terbutaline; diuretics, e.g. amiloride; hormones, e.g. cortisone, hydrocortisone or prednisolone; and therapeutic proteins and peptides, e.g. glucagon. Where appropriate the medicaments may be used in the form of salts (e.g as alkali metal or amine salts or as acid addition salts) or as esters (e.g. lower alkyl esters) to optimise the activity and/or stability of the medicament and/or to minimise the solubility of the medicament in the propellant.

Particularly preferred medicaments for administration using aerosol formulations in accordance with the invention include bronchodilators and anti-inflammatory steroids currently used in the treatment of asthma by inhalations therapy. Salbutamol (eg. as the sulphate), salmeterol (e.g. as the hydroxynaphthoate), beclomethasone esters (e.g. the dipropionate) or fluticasone esters (e.g. the propionate) are especially preferred medicaments for use in the formulations of the invention.

The surfactants for use in the invention will have no affinity for the propellant (that is to say they will contain no groups which have affinity with the propellant).

The surfactants must be physiologically acceptable upon administration by inhalation. Surfactants within this category include materials such as benzalkonium chloride, lecithin, oleic acid and sorbitan trioleate (Span$^R$85).

The use of substantially non-ionic surfactants which have reasonable solubility in substantially non-polar solvents is frequently advantageous since it facilitates coating of the medicament particles using solutions of surfactant in non-polar solvents in which the medicament has limited or minimal solubility.

Thus according to a further aspect of the invention the aerosol formulations may be prepared by slurrying particulate (e.g. micronised) medicament with a solution of a surfactant such as lecithin in a substantially non-polar solvent (e.g. a lower alkane such as isopentane or a chlorofluorocarbon such as trichlorofluoromethane), optionally homogenising the slurry (e.g. by sonication), removing the solvent and if necessary simultaneously and/or subsequently breaking up the resulting solid cake, and dispersing the thus-obtained surfactant-coated particulate medicament in the chosen propellant in an appropriate aerosol container, e.g. with the aid of sonication. It may be preferred to add the cosolvent after the coated medicament and propellant have been combined, in order to minimise any solubilising effects of the cosolvent and thereby enhance the stability of the dispersion. The process is desirably carried out under anhydrous conditions to obviate hydrate, formation.

The particle size of the finely-powdered medicament should be such as to permit inhalation of substantially all of the medicament into the bronchial system upon administration of the aerosol formulation and will thus be less than 100 microns, desirably less than 20 microns, and preferably in the range 2–10 microns, e.g. 2–5 microns.

The amount of surfactant employed in coating the particulate medicament is desirably in the range 0.01–10.0% w/w, preferably 0.05–5.0% w/w, relative to the medicament, and may advantageously be chosen such that a substantially monomolecular coating of surfactant is formed. The final aerosol formulation desirably contains 0.005–5.0% w/w, preferably 0.01–1.0% w/w, of coated medicament relative to the total weight of the formulation.

The following non-limitative Examples serve to illustrate the invention.

EXAMPLE 1

(A) Preparation of Lecithin-coated Salmeterol Hydroxynapthoate (a) Lecithin (Epikuron 145V-3.65 mg) was dissolved in a small amount of isopentane and the resulting solution was added to micronised salmeterol hydroxynaphthoate (0.5 g). Further isopentane (7.0 g total) was added to form a slurry, which was sonicated for 3 minutes. The resulting suspension was dried by evaporating the isopentane at ambient temperature in a fume cupboard, whereafter the resulting dried plug was roughly broken up and then dried further in a vacuum oven. The thus-obtained product was further broken up using a mortar and pestle to yield lecithin-coated salmeterol hydroxynaphthoate containing 0.73% w/w of lecithin relative to the salmeterol hydroxynaphthoate.

(b) The above procedure was repeated except that 6.10 mg of lecithin was employed, whereby a coated product containing 1.22% w/w of lecithin relative to the salmeterol hydroxynaphthoate was obtained.

(c) The above procedure was again repeated except that 7.80 mg of lecithin was employed, thereby yielding a coated product containing 1.56% w/w of lecithin relative to the salmeterol hydroxynaphthoate.

(B) Formulation of Lecithin-coated Salmeterol Hydroxynaphthoate in Ethanol-containing 1,1,1,2-Tetrafluoroethane (a) Samples of each of the products of Examples 1(A) (a)–(c) (9.1 mg) were weighed into aerosol cans containing dried ethanol (0.018 g–0.1% w/w of total fill weight) and 1,1,1,2-tetrafluoroethane (ca. 5 g). Further 1,1,1,2-tetrafluoroethane (total 18.2 g–99.95% w/w of total fill weight) was added to each can, whereafter suitable metering valves were crimped onto the cans, which were then each sonicated for 5 minutes. The resulting aerosols contained salmeterol in an amount equivalent to 240 actuations at 25 µg per actuation.

(b) The above procedure was repeated except that 0.091 g of dried ethanol was employed in each formulation, whereby aerosols containing 0.5% w/w ethanol and 99.45% w/w of propellant were obtained.

What is claimed is:

1. An aerosol formulation comprising:

(i) a hydrogen-containing fluorocarbon or chlorofluorocarbon propellant which is selected from the group consisting of $CH_2ClF$, $CClF_2$—$CHClF$, $CF_3$—$CHClF$, $CHF_2$—$CClF_2$, $CHClF$—$CHF_2$, $CF_3$—$CH_2Cl$, $CHF_2$—$CHF_2$, $CF_3$—$CH_2F$, $CClF_2$—$CH_3$, $CHF_2$—$CH_3$ and $CF_3CHFCF_3$;

(ii) a cosolvent having higher polarity than the propellant, which cosolvent is present in an amount of less than 1% w/w based upon the weight of propellant; and (iii) a medicament in particulate form, said medicament having a particle size of less than 100 µm and having a surface coating of a surfactant in an amount of from 0.05 to 5% w/w based upon the weight of the medicament, and wherein said surfactant has no affinity for said propellant.

2. A formulation as claimed in claim 1 wherein the propellant comprises 1,1,1,2-tetrafluoroethane or 1,1,1,2,3,3,3-heptafluoropropane.

3. A formulation as claimed in claim 1 wherein the propellant comprises 1,1,1,2-tetrafluoroethane.

4. A formulation as claimed in claim 1 which is substantially free of chlorofluorocarbons.

5. A formulation as claimed in claim 1 wherein the cosolvent is selected from the group consisting of an aliphatic alcohol or a polyol.

6. A formulation as claimed in claim 1 wherein the surfactant is selected from the group consisting of benzalkonium chloride, lecithin, oleic acid and sorbitan trioleate.

7. A formulation as claimed in claim 1 wherein the medicament is selected from the group consisting of salbutamol, salmeterol, beclomethasone esters or fluticasone esters.

* * * * *